(12) United States Patent
Soto Del Valle et al.

(10) Patent No.: US 10,751,065 B2
(45) Date of Patent: Aug. 25, 2020

(54) ANEURYSM DEVICE AND DELIVERY SYSTEM

(71) Applicant: DePuy Synthes Products, Inc., Raynham, MA (US)

(72) Inventors: Ariel Soto Del Valle, Raynham, MA (US); Lacey Gorochow, Raynham, MA (US); Juan Lorenzo, Raynham, MA (US)

(73) Assignee: DePuy Synthes Products, Inc., Raynham, MA (US)

( * ) Notice: Subject to any disclaimer, the term of this patent is extended or adjusted under 35 U.S.C. 154(b) by 245 days.

(21) Appl. No.: 15/852,829

(22) Filed: Dec. 22, 2017

(65) Prior Publication Data
US 2019/0192167 A1 Jun. 27, 2019

(51) Int. Cl.
| | |
|---|---|
| A61B 17/12 | (2006.01) |
| A61F 2/852 | (2013.01) |
| A61F 2/90 | (2013.01) |
| A61B 90/00 | (2016.01) |
| A61F 2/966 | (2013.01) |
| A61M 25/00 | (2006.01) |

(52) U.S. Cl.
CPC .. *A61B 17/12172* (2013.01); *A61B 17/12031* (2013.01); *A61B 17/12113* (2013.01); *A61F 2/852* (2013.01); *A61F 2/90* (2013.01); *A61B 2017/12054* (2013.01); *A61B 2090/3983* (2016.02); *A61F 2002/9665* (2013.01); *A61F 2250/0023* (2013.01); *A61M 2025/0042* (2013.01)

(58) Field of Classification Search
CPC ........ A61B 17/12022; A61B 17/12031; A61B 17/12109; A61B 17/12113; A61B 17/12168; A61B 17/12172
See application file for complete search history.

(56) References Cited

U.S. PATENT DOCUMENTS

| | | |
|---|---|---|
| 6,391,037 B1 | 5/2002 | Greenhalgh |
| 6,506,204 B2 | 1/2003 | Mazzocchi |
| 8,777,974 B2 | 7/2014 | Amplatz et al. |
| 8,974,512 B2 | 3/2015 | Aboytes et al. |

(Continued)

FOREIGN PATENT DOCUMENTS

| | | |
|---|---|---|
| WO | 2005/117718 A1 | 12/2005 |
| WO | 2015/160721 A1 | 10/2015 |
| WO | 2015/171268 A2 | 11/2015 |

*Primary Examiner* — Todd J Scherbel
(74) *Attorney, Agent, or Firm* — Troutman Pepper Hamilton Sanders LLP

(57) ABSTRACT

The present disclosure relates to a braid for treating an aneurysm. The braid can include a first radially expandable segment operable to move from a collapsed state within a microcatheter to a deployed state distal of the microcatheter. The first radially expandable segment can be capable of radially expanding to form an outer occlusive sack in the aneurysm in the deployed state. The braid can also include a second radially expandable segment operable to move from the collapsed state within the microcatheter to the deployed state distal of the microcatheter, wherein the second radially expandable segment is capable of radially expanding inside the outer occlusive sack to form an inner occlusive sack in the outer occlusive sack in the deployed state.

16 Claims, 12 Drawing Sheets

(56) References Cited

U.S. PATENT DOCUMENTS

| | | |
|---|---|---|
| 8,998,947 B2 | 4/2015 | Aboytes et al. |
| 9,055,948 B2 | 6/2015 | Jaeger et al. |
| 9,232,992 B2 | 1/2016 | Heidner et al. |
| 9,314,326 B2 | 4/2016 | Wallace et al. |
| 9,532,792 B2 | 1/2017 | Galdonik et al. |
| 9,532,873 B2 | 1/2017 | Kelley |
| 9,533,344 B2 | 1/2017 | Monetti et al. |
| 9,539,011 B2 | 1/2017 | Chen et al. |
| 9,539,022 B2 | 1/2017 | Bowman |
| 9,539,122 B2 | 1/2017 | Burke et al. |
| 9,539,382 B2 | 1/2017 | Nelson |
| 9,549,830 B2 | 1/2017 | Bruszewski et al. |
| 9,554,805 B2 | 1/2017 | Tompkins et al. |
| 9,561,125 B2 | 2/2017 | Bowman et al. |
| 9,572,982 B2 | 2/2017 | Burnes et al. |
| 9,579,484 B2 | 2/2017 | Barnell |
| 9,585,642 B2 | 3/2017 | Dinsmoor et al. |
| 9,615,832 B2 | 4/2017 | Bose et al. |
| 9,615,951 B2 | 4/2017 | Bennett et al. |
| 9,622,753 B2 | 4/2017 | Cox |
| 9,636,115 B2 | 5/2017 | Henry et al. |
| 9,636,439 B2 | 5/2017 | Chu et al. |
| 9,642,675 B2 | 5/2017 | Werneth et al. |
| 9,655,633 B2 | 5/2017 | Leynov et al. |
| 9,655,645 B2 | 5/2017 | Staunton |
| 9,655,989 B2 | 5/2017 | Cruise et al. |
| 9,662,129 B2 | 5/2017 | Galdonik et al. |
| 9,662,238 B2 | 5/2017 | Dwork et al. |
| 9,662,425 B2 | 5/2017 | Lilja et al. |
| 9,668,898 B2 | 6/2017 | Wong |
| 9,675,477 B2 | 6/2017 | Thompson |
| 9,675,782 B2 | 6/2017 | Connolly |
| 9,676,022 B2 | 6/2017 | Ensign |
| 9,692,557 B2 | 6/2017 | Murphy |
| 9,693,852 B2 | 7/2017 | Lam et al. |
| 9,700,262 B2 | 7/2017 | Janik et al. |
| 9,700,399 B2 | 7/2017 | Acosta-Acevedo |
| 9,717,421 B2 | 8/2017 | Griswold et al. |
| 9,717,500 B2 | 8/2017 | Tieu et al. |
| 9,717,502 B2 | 8/2017 | Teoh et al. |
| 9,724,103 B2 | 8/2017 | Cruise et al. |
| 9,724,526 B2 | 8/2017 | Strother et al. |
| 9,750,565 B2 | 9/2017 | Bloom et al. |
| 9,757,260 B2 | 9/2017 | Greenan |
| 9,764,111 B2 | 9/2017 | Gulachenski |
| 9,770,251 B2 | 9/2017 | Bowman |
| 9,770,577 B2 | 9/2017 | Li |
| 9,775,621 B2 | 10/2017 | Tompkins et al. |
| 9,775,706 B2 | 10/2017 | Paterson |
| 9,775,732 B2 | 10/2017 | Khenansho |
| 9,788,800 B2 | 10/2017 | Mayoras, Jr. |
| 9,795,391 B2 | 10/2017 | Saatchi et al. |
| 9,801,980 B2 | 10/2017 | Karino et al. |
| 9,808,599 B2 | 11/2017 | Bowman |
| 9,833,252 B2 | 12/2017 | Sepetka |
| 9,833,604 B2 | 12/2017 | Lam |
| 9,833,625 B2 | 12/2017 | Waldhauser et al. |
| 2003/0171739 A1 | 9/2003 | Murphy et al. |
| 2005/0251200 A1 | 11/2005 | Porter |
| 2006/0052816 A1 | 3/2006 | Bates et al. |
| 2006/0064151 A1 | 3/2006 | Guterman et al. |
| 2008/0281350 A1 | 11/2008 | Sepetka et al. |
| 2010/0023046 A1 | 1/2010 | Heidner et al. |
| 2010/0324649 A1 | 12/2010 | Mattsson et al. |
| 2011/0152993 A1 | 6/2011 | Marchand et al. |
| 2012/0283768 A1 | 11/2012 | Cox et al. |
| 2013/0204351 A1 | 8/2013 | Cox et al. |
| 2014/0135812 A1 | 5/2014 | Divino et al. |
| 2014/0200607 A1 | 7/2014 | Sepetka et al. |
| 2014/0277013 A1* | 9/2014 | Sepetka ............... A61B 17/221 606/159 |
| 2015/0209050 A1 | 7/2015 | Aboytes et al. |
| 2015/0272589 A1 | 10/2015 | Lorenzo |
| 2015/0342613 A1 | 12/2015 | Aboytes et al. |
| 2015/0374483 A1 | 12/2015 | Janardhan et al. |
| 2016/0022445 A1 | 1/2016 | Ruvalcaba et al. |
| 2016/0249934 A1 | 9/2016 | Hewitt et al. |
| 2017/0007264 A1 | 1/2017 | Cruise et al. |
| 2017/0007265 A1 | 1/2017 | Guo et al. |
| 2017/0020670 A1 | 1/2017 | Murray et al. |
| 2017/0020700 A1 | 1/2017 | Bienvenu |
| 2017/0027640 A1 | 2/2017 | Kunis et al. |
| 2017/0027692 A1 | 2/2017 | Bonhoeffer |
| 2017/0027725 A1 | 2/2017 | Argentine |
| 2017/0035436 A1 | 2/2017 | Morita |
| 2017/0035567 A1 | 2/2017 | Duffy |
| 2017/0042548 A1 | 2/2017 | Lam |
| 2017/0049596 A1 | 2/2017 | Schabert |
| 2017/0071737 A1 | 3/2017 | Kelley |
| 2017/0072452 A1 | 3/2017 | Monetti et al. |
| 2017/0079661 A1* | 3/2017 | Bardsley .......... A61B 17/12186 |
| 2017/0079662 A1* | 3/2017 | Rhee ................ A61B 17/12172 |
| 2017/0079671 A1 | 3/2017 | Morero |
| 2017/0079680 A1 | 3/2017 | Bowman |
| 2017/0079766 A1 | 3/2017 | Wang |
| 2017/0079767 A1 | 3/2017 | Leon-Yip |
| 2017/0079812 A1 | 3/2017 | Lam et al. |
| 2017/0079817 A1 | 3/2017 | Sepetka |
| 2017/0079819 A1 | 3/2017 | Pung et al. |
| 2017/0079820 A1 | 3/2017 | Lam et al. |
| 2017/0086851 A1 | 3/2017 | Wallace |
| 2017/0086996 A1 | 3/2017 | Peterson et al. |
| 2017/0095259 A1 | 4/2017 | Tompkins et al. |
| 2017/0100126 A1 | 4/2017 | Bowman et al. |
| 2017/0100141 A1 | 4/2017 | Morero et al. |
| 2017/0100143 A1 | 4/2017 | Granfield |
| 2017/0100183 A1 | 4/2017 | Iaizzo |
| 2017/0113023 A1 | 4/2017 | Steingisser et al. |
| 2017/0147765 A1 | 5/2017 | Mehta |
| 2017/0151032 A1 | 6/2017 | Loisel |
| 2017/0165062 A1 | 6/2017 | Rothstein |
| 2017/0165065 A1 | 6/2017 | Rothstein |
| 2017/0165454 A1 | 6/2017 | Tuohy |
| 2017/0172581 A1 | 6/2017 | Bose et al. |
| 2017/0172766 A1 | 6/2017 | Vong et al. |
| 2017/0172772 A1 | 6/2017 | Khenansho |
| 2017/0189033 A1 | 7/2017 | Sepetka et al. |
| 2017/0189035 A1 | 7/2017 | Porter |
| 2017/0215902 A1 | 8/2017 | Leynov et al. |
| 2017/0216484 A1 | 8/2017 | Cruise et al. |
| 2017/0224350 A1 | 8/2017 | Shimizu et al. |
| 2017/0224355 A1 | 8/2017 | Bowman et al. |
| 2017/0224467 A1 | 8/2017 | Piccagli et al. |
| 2017/0224511 A1 | 8/2017 | Dwork et al. |
| 2017/0224953 A1 | 8/2017 | Tran et al. |
| 2017/0231749 A1 | 8/2017 | Perkins et al. |
| 2017/0252064 A1 | 9/2017 | Staunton |
| 2017/0265983 A1 | 9/2017 | Lam et al. |
| 2017/0281192 A1 | 10/2017 | Tieu et al. |
| 2017/0281331 A1 | 10/2017 | Perkins et al. |
| 2017/0281344 A1 | 10/2017 | Costello |
| 2017/0281909 A1 | 10/2017 | Northrop et al. |
| 2017/0281912 A1 | 10/2017 | Melder |
| 2017/0290593 A1 | 10/2017 | Cruise et al. |
| 2017/0290654 A1 | 10/2017 | Sethna |
| 2017/0296324 A1 | 10/2017 | Argentine |
| 2017/0296325 A1 | 10/2017 | Marrocco et al. |
| 2017/0303939 A1 | 10/2017 | Greenhalgh |
| 2017/0303942 A1 | 10/2017 | Greenhalgh et al. |
| 2017/0303947 A1 | 10/2017 | Greenhalgh |
| 2017/0303948 A1 | 10/2017 | Wallace et al. |
| 2017/0304041 A1 | 10/2017 | Argentine |
| 2017/0304097 A1 | 10/2017 | Corwin et al. |
| 2017/0304595 A1 | 10/2017 | Nagasrinivasa |
| 2017/0312109 A1 | 11/2017 | Le |
| 2017/0312484 A1 | 11/2017 | Shipley et al. |
| 2017/0316561 A1 | 11/2017 | Helm et al. |
| 2017/0319826 A1 | 11/2017 | Bowman |
| 2017/0333228 A1 | 11/2017 | Orth et al. |
| 2017/0333236 A1 | 11/2017 | Greenan |
| 2017/0333678 A1 | 11/2017 | Bowman |
| 2017/0340383 A1 | 11/2017 | Bloom et al. |

(56) References Cited

U.S. PATENT DOCUMENTS

2017/0348014 A1    12/2017   Wallace
2017/0348514 A1    12/2017   Guyon et al.
2018/0242979 A1     8/2018   Lorenzo

* cited by examiner

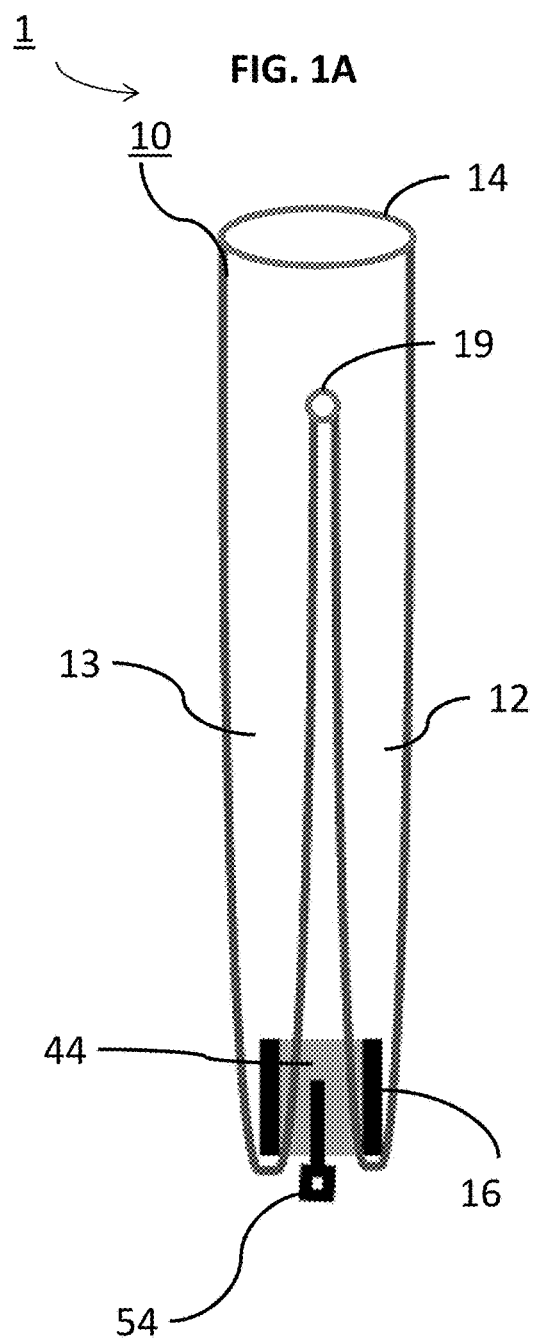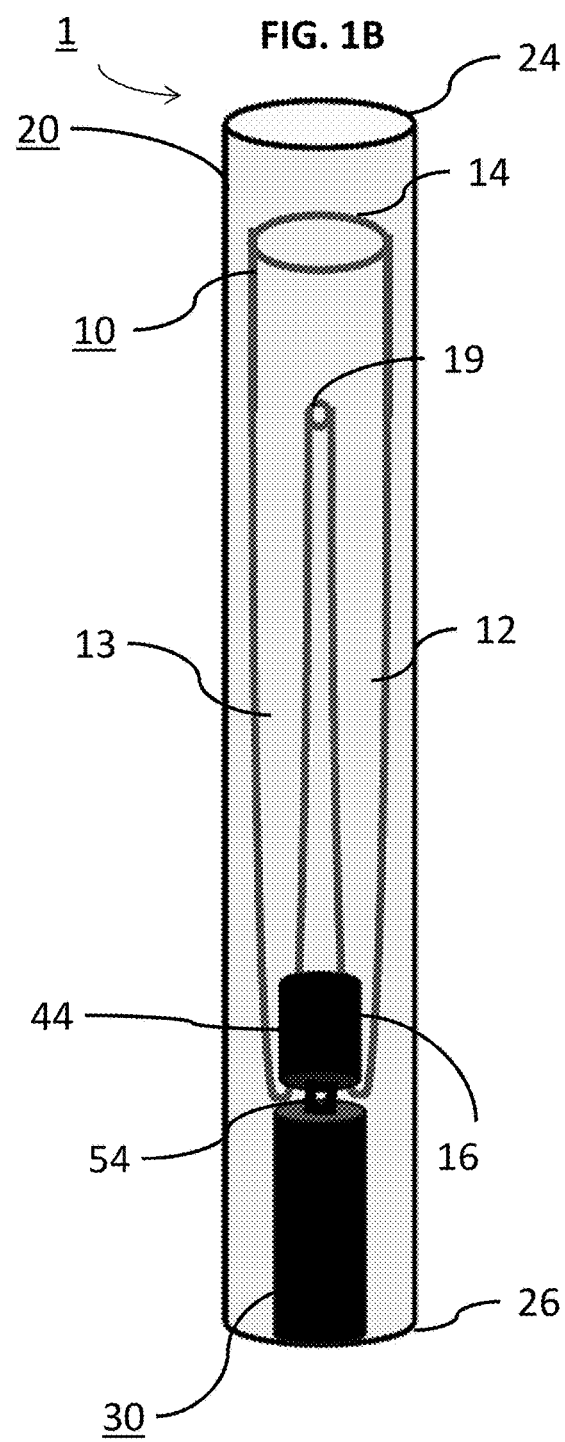

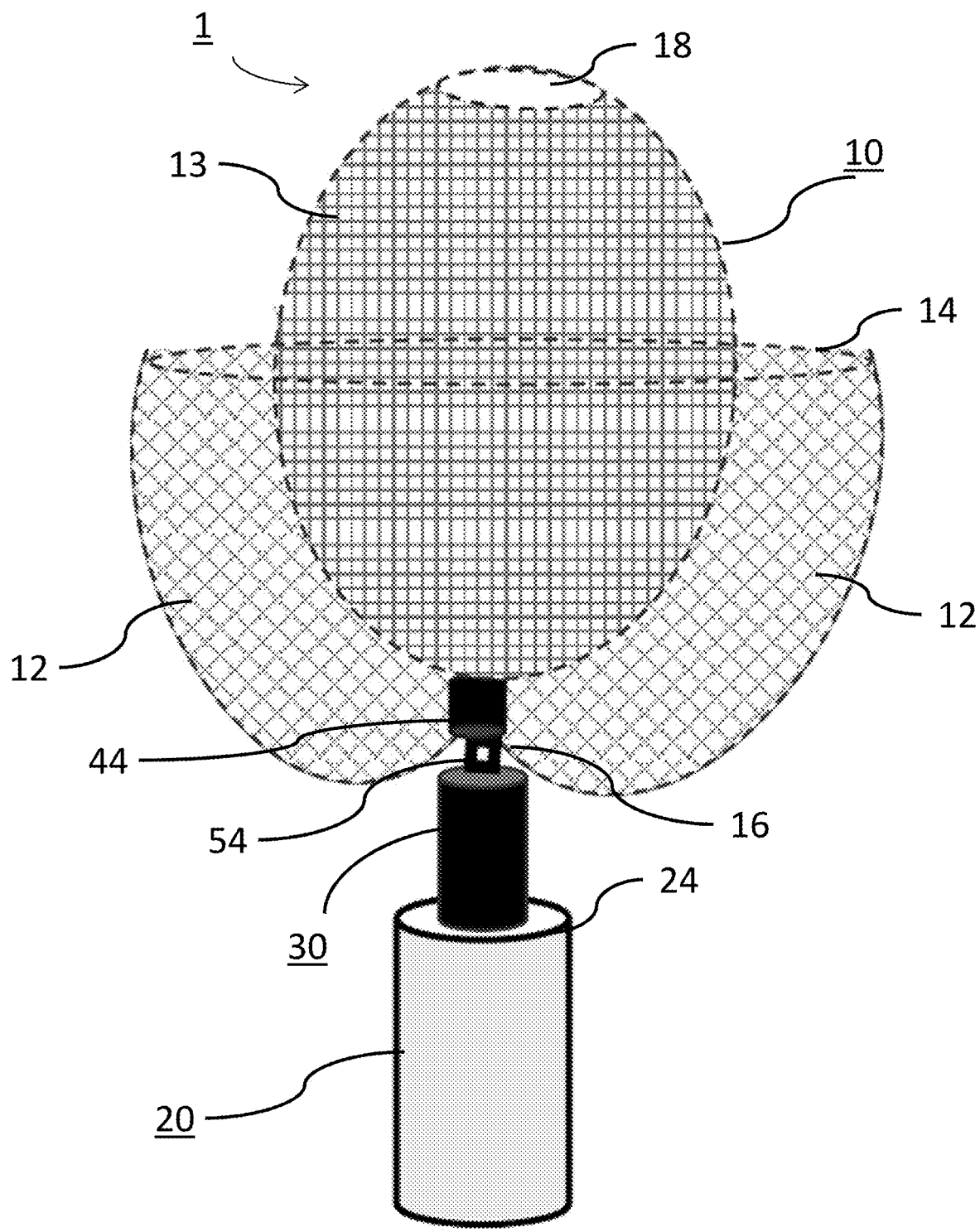

1105 — slidably positioning a delivery tube within a microcatheter;

1110 — positioning a radially expandable braid within the microcatheter, the braid being in a collapsed state within the microcatheter and comprising a distal end and a proximal end 1115 — attaching the proximal end of the braid to the distal end of the delivery tube 1120 — selectively positioning the microcatheter, the delivery tube, and the braid into vasculature of the aneurysm 1125 — distally sliding the braid from the microcatheter, by the delivery tube, towards the aneurysm 1130 — distally pushing the braid, by the delivery tube, into the aneurysm whereby a first radially expandable segment of the braid radially expands to form an outer occlusive sack, the outer occlusive sack being operable to lay across a neck of the aneurysm 1135 — further distally pushing the braid thereby expanding an inner layer of the braid inside of the outer occlusive sack while distally pushing the outer occlusive sack against the aneurysm wall and aneurysm neck 1140 — releasing the braid, including the outer and inner occlusive sacks, and withdrawing the delivery tube and the microcatheter from the aneurysm

FIG. 12

1200

- 1205: positioning a radially expandable braid within vasculature of the aneurysm
- 1210: forming a first radially expandable segment of the braid with a porosity lower than a porosity of a second radially expandable segment;
- 1215: distally pushing the braid into the aneurysm whereby the first radially expandable segment radially expands to form an outer occlusive sack
- 1220: further distally pushing the braid thereby expanding the second radially expandable segment inside of the outer occlusive sack
- 1225: positioning the first radially expandable segment adjacent or in communication with a neck of the aneurysm
- 1230: deflecting, diverting or slowing flow into the aneurysm across the neck of the aneurysm when the outer occlusive sack is formed across the neck and the inner occlusive sack is formed therein

ANEURYSM DEVICE AND DELIVERY SYSTEM

FIELD

This disclosure relates to medical instruments, and more particularly, delivery systems for aneurysm therapy.

BACKGROUND

Aneurysms can be complicated and difficult to treat. For example, treatment access may be limited or unavailable when an aneurysm is located proximate critical tissues. Such factors are of concern with cranial aneurysms due to the brain tissue surrounding cranial vessels the corresponding limited treatment access.

Prior solutions have included endovascular treatment access whereby an internal volume of the aneurysm sac is removed or excluded from arterial blood pressure and flow. In this respect, because the interior walls of the aneurysm may continue being subjected to flow of blood and related pressure, aneurysm rupture remains possible.

Alternative to endovascular or other surgical approaches can include occlusive devices. Such devices have typically incorporated multiple embolic coils that are delivered to the vasculature using microcatheter delivery systems. For example, when treating cranial aneurysms, a delivery catheter with embolic coils is typically first inserted into non-cranial vasculature through a femoral artery in the hip or groin area. Thereafter, the catheter is guided to a location of interest within the cranium. The sac of the aneurysm can then be filled with the embolic material to create a thrombotic mass that protects the arterial walls from blood flow and related pressure. However, such occlusive devices do have certain shortcomings, including the fact that volume they can fill is somewhat permanent due to the thrombotic mass delivered therein.

One particular type of occlusive approach endeavors to deliver and treat the entrance or "neck" of the aneurysm as opposed to the volume of the aneurysm. In such "neck" approaches, by minimizing blood flow across the neck, then a venostasis in the aneurysm may be achieved. In turn, a thrombotic mass may naturally form without having to deliver embolic materials, as previously described. This is preferable to masses formed from embolic material since a natural mass can improve healing by reducing possible distention from arterial walls and permits reintegration into the original parent vessel shape along the neck plane of the aneurysm. It is understood that the neck plane is an imaginary surface where the inner most layer of the parent wall would be but for the aneurysm. However, neck-occlusive approaches are not without drawbacks. It is typical for neck-occlusive approaches to fail to impede flow into blood vessels while also blocking the aneurysm neck in the parent vessel. This can unintentionally lead to severe damage if the openings of the vessels are blocked. Furthermore, embolic coils do not always effectively treat aneurysms as re-canalization of the aneurysm and/or coil compaction can occur over time.

It is therefore desirable to have a device which easily, accurately, and safely occludes a neck of an aneurysm or other arterio-venous malformation in a parent vessel without blocking flow into perforator vessels communicating with the parent vessel.

SUMMARY

In some aspects, the present disclosure relates to a braid for treating an aneurysm. The braid can include a lumen with a distal end opposite a proximal end.

In one embodiment, an occlusive device for treating an aneurysm is disclosed. The device can include a braid that is translatably disposable within a microcatheter from a collapsed state to a deployed state. The braid can include a distal end and a proximal end. In the deployed state, the braid can include an outer occlusive sack capable of pushing against an aneurysm wall of the aneurysm. In the deployed state, the braid can also include an inner occlusive sack disposed inside and/or internally overlaid with the outer occlusive sack.

In some embodiments, a porosity of the inner occlusive sack can be greater than a porosity of the outer occlusive sack.

In some embodiments, in the deployed state, the outer occlusive sack is capable of sealing against the neck of the aneurysm.

In some embodiments, distally translating the braid after the outer occlusive sack is formed causes an inner layer of the braid inside of the outer occlusive sack to radially expand inside the outer occlusive sack and form the inner occlusive sack. The inner layer of the braid can be capable of radially expanding inside the outer occlusive sack while the outer occlusive sack is pushed against the aneurysm wall and aneurysm neck. In some embodiments, a marker band can be in communication with the proximal end of the braid. The inner layer that radially expands inside the outer occlusive sack can be formed by folding the proximal end over the marker band.

In some embodiments, in the deployed state, the braid is detachable from a delivery system in the aneurysm. The delivery system can include a microcatheter and a delivery tube with a distal end and a proximal end. The distal end of the delivery tube can be detachably connected to the proximal end of the braid. In this regard, the delivery tube can be translatably disposable within the microcatheter. The delivery tube can be capable of distally translating the braid within the microcatheter from the collapsed state to the deployed state.

In some embodiments, the outer occlusive sack is a collapsible cage-like vaso-occlusive structure.

In some embodiments, the outer occlusive sack can have fewer wire segments than the inner occlusive sack.

In some embodiments, the device can be in communication with an imaging device capable of imaging the outer and/or inner occlusive sacks with respect to the aneurysm. An orientation and/or packing density of the outer and/or inner occlusive sacks can be adjustable by the braid being distally or proximally moved.

In some embodiments, a braid for treating an aneurysm is disclosed. The braid can include a first radially expandable segment operable to move from a collapsed state within a microcatheter to a deployed state distal of the microcatheter. The first radially expandable segment can be capable of radially expanding to form an outer occlusive sack in the aneurysm in the deployed state that is sealable against a neck of the aneurysm. The braid can also include a second radially expandable segment operable to move from the collapsed state within the microcatheter to the deployed state distal of the microcatheter. The second radially expandable segment can be capable of radially expanding inside the outer occlusive sack to form an inner occlusive sack in the outer occlusive sack in the deployed state.

In some embodiments, the braid is detachably deployable by a delivery system to an aneurysm.

In some embodiments, the braid can also include a buckle portion disposed between the first and second radially expandable segments, the buckle portion permitting the inner occlusive sack to be formed within, overlaid with, and/or expand (e.g. radially) in the outer occlusive sack when positioned across the neck of the aneurysm.

In some embodiments, dimensions of interstices of the braid vary at the proximal end versus the distal end so that a porosity of the outer occlusive sack is less than a porosity of the inner occlusive sack.

In some embodiments, a method of occluding an aneurysm is disclosed. The method can include positioning a radially expandable braid into vasculature of the aneurysm; forming a first radially expandable segment of the braid with a porosity lower than a porosity of a second radially expandable segment; distally pushing the braid into the aneurysm whereby the first radially expandable segment radially expands to form an outer occlusive sack; further distally pushing the braid thereby expanding the second radially expandable segment inside of the outer occlusive sack; positioning the first radially expandable segment adjacent or in communication with a neck of the aneurysm; deflecting, diverting or slowing flow into the aneurysm across the neck of the aneurysm when the outer occlusive sack is formed across the neck and the inner occlusive sack is formed therein.

In some embodiments, a method of delivering an occlusive device to an aneurysm is disclosed. The method includes slidably positioning a delivery tube within a microcatheter; positioning a radially expandable braid within the microcatheter, the braid being in a collapsed state within the microcatheter and comprising a distal end and a proximal end; attaching the proximal end of the braid to the distal end of the delivery tube; selectively positioning the microcatheter, the delivery tube, and the braid into vasculature of the aneurysm; distally sliding the braid from the microcatheter, by the delivery tube, towards the aneurysm; distally pushing the braid, by the delivery tube, into the aneurysm whereby a first radially expandable segment of the braid radially expands to form an outer occlusive sack, the outer occlusive sack being operable to lay across a neck of the aneurysm; further distally pushing the braid thereby expanding a second radially expandable segment of the braid inside of the outer occlusive sack while distally pushing the outer occlusive sack against the aneurysm wall and the neck of the aneurysm; and releasing the braid, including the outer and inner occlusive sacks, and withdrawing the delivery tube and the microcatheter from the aneurysm.

In some embodiments, the method also includes forming the first radially expandable segment with a porosity lower than a porosity of the second radially expandable segment; positioning the first radially expandable segment adjacent or in communication with a neck of the aneurysm; and deflecting, diverting or slowing flow into the aneurysm across the neck of the aneurysm when the outer occlusive sack is formed across the neck and the inner occlusive sack is formed therein.

In some embodiments, the inner occlusive sack comprises an inner layer of the braid. The outer and inner occlusive sacks, when formed in certain embodiments, include a predetermined packing density range.

In some embodiments, the method includes imaging the outer occlusive sack and/or inner occlusive sack with respect to the aneurysm; determining whether the aneurysm is occluded by the outer occlusive sack and/or inner occlusive sack; and distally or proximally sliding the braid to adjust the outer occlusive sack and/or inner occlusive sack to occlude the aneurysm.

Other aspects and features of the present disclosure will become apparent to those of ordinary skill in the art, upon reviewing the following detailed description in conjunction with the accompanying figures.

BRIEF DESCRIPTION OF THE DRAWINGS

Reference will now be made to the accompanying drawings, which are not necessarily drawn to scale.

FIG. 1A depicts an example occlusive device of this disclosure in a collapsed state.

FIG. 1B depicts an example occlusive device of this disclosure in a collapsed state within an example microcatheter.

FIG. 2 depicts an example occlusive device of this disclosure, wherein the braid is being deployed.

FIG. 11 is a flow diagram for a method of delivering an occlusive device;

FIG. 12 is a flow diagram for a method of delivering an occlusive device.

DETAILED DESCRIPTION

Figure 3:
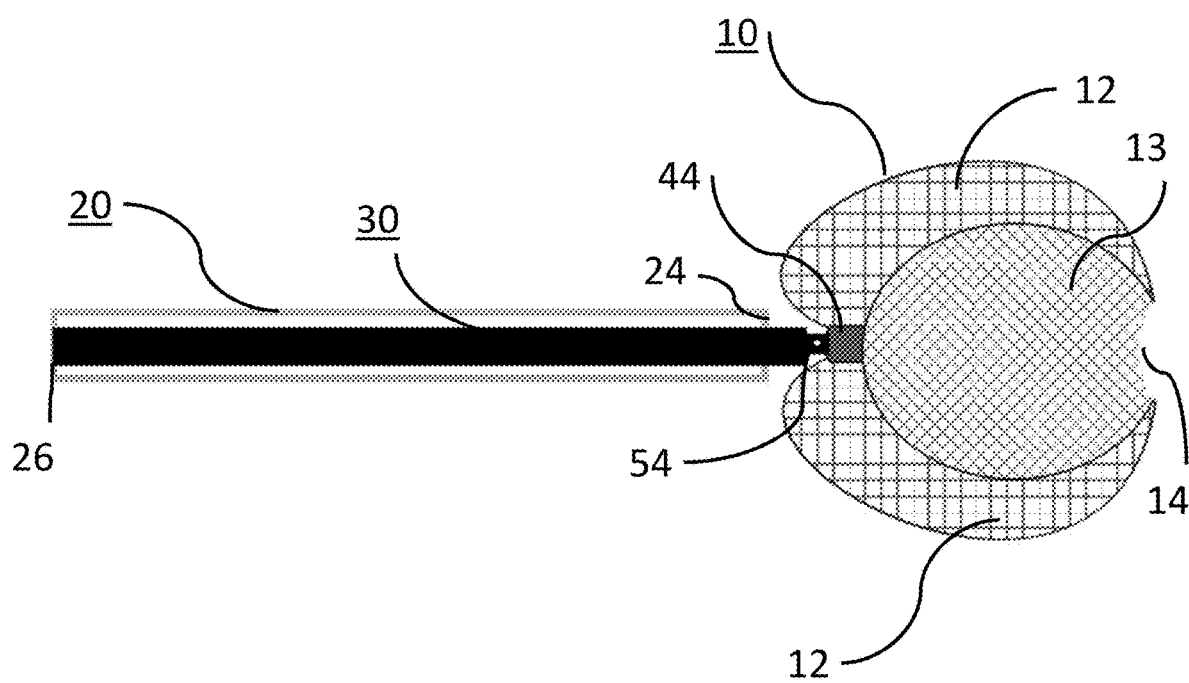
FIG. 3 is a schematic side view of an exemplary delivery system with an occlusive device in a deployed state.

Although example embodiments of the disclosed technology are explained in detail herein, it is to be understood that other embodiments are contemplated. Accordingly, it is not intended that the disclosed technology be limited in its scope to the details of construction and arrangement of components set forth in the following description or illustrated in the drawings. The disclosed technology is capable of other embodiments and of being practiced or carried out in various ways.

It must also be noted that, as used in the specification and the appended claims, the singular forms "a," "an" and "the" include plural referents unless the context clearly dictates otherwise. By "comprising" or "containing" or "including" it is meant that at least the named compound, element, particle, or method step is present in the composition or article or method, but does not exclude the presence of other compounds, materials, particles, method steps, even if the other such compounds, material, particles, method steps have the same function as what is named.

In describing example embodiments, terminology will be resorted to for the sake of clarity. It is intended that each term contemplates its broadest meaning as understood by those skilled in the art and includes all technical equivalents that operate in a similar manner to accomplish a similar purpose. It is also to be understood that the mention of one or more steps of a method does not preclude the presence of additional method steps or intervening method steps between those steps expressly identified. Steps of a method may be performed in a different order than those described herein without departing from the scope of the disclosed technology. Similarly, it is also to be understood that the mention of one or more components in a device or system does not preclude the presence of additional components or intervening components between those components expressly identified.

As discussed herein, vasculature can be that of any "subject" or "patient" including of any human or animal. It should be appreciated that an animal may be a variety of any applicable type, including, but not limited thereto, mammal, veterinarian animal, livestock animal or pet type animal, etc. As an example, the animal may be a laboratory animal specifically selected to have certain characteristics similar to a human (e.g., rat, dog, pig, monkey, or the like). It should be appreciated that the subject may be any applicable human patient, for example.

As discussed herein, "operator" may include a doctor, surgeon, or any other individual or delivery instrumentation associated with delivery of a braid body to the vasculature of a subject.

Cerebrovascular aneurysms are known to be treated using embolic coils, which are delivered to the aneurysm sack via a microcatheter and detached in situ. It is understood that "packing density" is the volume of the aneurysm sack occupied by the coil mass. In previous coil approaches, multiple coils (e.g. five coils) have been used to pack the aneurysms and the packing density can typically range between 20-25%. The herein disclosed device improves on prior approaches by being operable to seal the aneurysm neck and pack the aneurysm to a higher packing density while avoiding risk of aneurysm rupture during package.

In previous embolic-based approaches, packing the aneurysm required in placement of coils into the aneurysm sack until the aneurysm obtained the desired packing density to occlude the aneurysm. However, obtaining such a density without risk of rupture was difficult, unsafe, and aneurysm morphology (e.g. wide neck, bifurcation, etc.), and the like, rendered it difficult, if not impossible, for an operator to re-position the coils once delivered and installed on site. Furthermore, aneurysms treated with multiple coils often reanalyze or compact as a result of poor coiling, lack of coverage across the aneurysm neck, as a result of flow, or even aneurysm size.

Relatedly, flow diverters that are deployed across the aneurysm neck can alter the flow of blood into the aneurysm. An example flow diverter can be a braided device with relatively low porosity. Over time, the aneurysms can heal by sealing the aneurysm neck with a high rate of success. However, flow diversion technology is not without limitations. Challenges include placement of the devices intravascularly due to vessel morphology, vessel tortuosity, or braid malposition. In addition, patients receiving a flow diverter must be on anticoagulation medicine for an extended period to prevent vessel thrombosis. Intrasaccular devices also aim to cut circulation into the aneurysm while minimizing the amount of metal in the vessel and significantly cutting, or eliminating the need for coagulation medication. These types of devices may also be easier to track and/or deploy at the lesion site.

The occlusive device 1 disclosed herein addresses these and other drawbacks of previous approaches. Turning to FIG. 1A, an example occlusive device 1 of this disclosure is shown in a collapsed state prior to being arranged with a microcatheter 20. FIG. 1B depicts the occlusive device of FIG. 1A arranged in the collapsed state within the microcatheter 20. As shown, device 1 can include a braid 10 formed from multiple self-expanding multi-filament segments that can be formed from a mesh. For example, braid 10 can include a first radially expandable segment 12 associated with an outer occlusive sack and a second radially expandable segment 13 associated with an inner occlusive sack. Braid 10 can also have a distal end 14 associated with segment 12, a distal end 18 associated with segment 13, and a proximal end 16. Each of ends 14 and 18 can be opened.

The mesh of braid 10 can be defined by one or more mesh patterns, one or more discrete mesh portions, and/or one or more mesh openings defined by braided filaments. For example, the mesh of braid 10 can include a porosity region associated with an outer occlusive sack formed by braid 10 and another porosity region associated with an inner occlusive sack configured to expand and/or internally overlay the outer occlusive sack. The inner occlusive sack can have a higher porosity than the outer occlusive sack. For example, the mesh of braid 10 shown in FIGS. 1A and 1B can include a different porosity region associated with each of segments 12, 13. Each of segments 12, 13 can be radially expandable and capable of being disposed inside microcatheter 20 in a collapsed state. Segment 12 can be an expandable, outer shell while segment 13 can be an inner, expandable shell. Each of segments 12, 13 can be heat shaped to spherical, saddled, ellipsoid shaped, or any other shape, as shown in FIGS. 1-2. Though only segments 12, 13 are depicted, any number of segments and corresponding sacks could be included as needed or required. Each of segments 12, 13 can be capable of being moved from the collapsed state to a deployed state.

In practice, the porosity of segment 12 can permit segment 12 to take on many shapes prior, during, or after delivery to aneurysm A. For example, the porosity of segment 12 can be relatively low to permit it to flexibly conform to a plurality of different shaped aneurysms. Segment 12 can have porosity less than the porosity of segment 13 based on differing aperture sizes. The porosities associated with segments 12, 13 and/or any other region or segment of braid 10 can also include filaments having a different shape and/or pick count than the filaments in the other porosity regions.

The mesh of braid 10 can be comprised of a tube that is closed at one end (e.g. proximal end 16) and/or opened at distal ends 14 and 18 and be made of several materials such as deposited thin films. The mesh of braid 10 can include multiple wires, for example from 4 to 96 wires. The number of wires can be a factor in controlling material properties of the braid 10, including the porosity, shape in the deployed state, flexibility, stiffness, and the like. The combination of the one or more sacks internally overlaid with an outer occlusive sack can be taken into account when determining the number of wires of the mesh of braid 10 since one sack is inside the other. Fewer wires of the mesh of braid 10 can be used as a whole and still result in a high packing density when combined.

The diameter of the braid 10, and the braid wire count can vary depending the diameter of the device needed to treat the aneurysm, and/or the desired porosity. For example, the distal end 14 of segment 12 can be an open end with a first diameter. The distal end 18 of segment 13 can be an open end with a second diameter that is less than the first diameter in the deployed state. The braid angle of the braid 10 can also be fixed, or vary along the length of braid 10 to create different porosity therealong. For example, to induce or facilitate formation of the predetermined shape and strength of the occlusive sacks of segments 12 and 13, ends 14 and 18 may be more pliable than end 16, or vice versa, and other segments of braid 10 may vary from most pliable on or about end 14 and/or end 18 and less pliable on or about end 16. In some embodiments, ends 14, 18 can be looped as shown, which is particularly advantageous to ensure that the braid 10 is atraumatic when in contact with the dome D of aneurysm A.

The number of wires, braid angle, patterns, or the like, can be used to define the porosities of segments 12, 13. The wires of braid 10 can be made from nitinol with interwoven platinum filaments for radiopacity, or Drawn Filled Tube (DFT) Nitinol with 10 to 40% Platinum. The wires can be made from a nickel-titanium alloy, cobalt chromium alloys, Stainless Steel, Tantalum, and/or other alloys, and/or any other suitable biocompatible materials, or combination of these materials. Also, these materials can be absorbable or non-absorbable by the patient over time. In this respect, the first porosity associated with segment 12 can be less than the second porosity associated with segment 13. Arranging segments 12, 13 in the deployed state, varying the braid properties, and/or positioning segment 12 adjacent or in communication with a neck of the aneurysm can facilitate inversion and/or deflect, divert or slow flow into the aneurysm. Material properties of segments 12, 13 can differ in other respects as well, as needed or required, including heat treatment or covering.

The apertures in the mesh of braid 10 can also create a substantially unitary frame work or mesh. Thus, the apertures may be of any size, shape, or porosity, and may be uniformly or randomly spaced throughout the wall of the mesh of braid 10. The apertures can provide the tubular element of braid 10 with flexibility and also assist in the transformation of the mesh from the collapsed state to the expanded, deployed state, and vice versa.

As shown in FIG. 1B and FIG. 2, the delivery system 40 can include the microcatheter 20 with a delivery tube 30 slideably disposed therein. The microcatheter 20 can be pre-placed at the level of the aneurysm neck and used to track the device to the aneurysm. The microcatheter 20 size can be selected in consideration of the size, shape, and directionality of the aneurysm or features through which the microcatheter 20 must pass to get to the treatment site. The microcatheter 20 may have a total usable length anywhere from 80 centimeters to 170 centimeters. The microcatheter 20 may have an inner diameter ID of anywhere between 0.015 and 0.032 inches. The outer diameter OD may also range in size and may narrow at either its proximal end or distal end. At its proximal end 26, the microcatheter 20 may be attached to a surgical device, and at its distal end 24 may be operable to positioned at the neck of the aneurysm A. While the distal end 24 of the microcatheter 20 as shown contains the braid 10, the end 24 may be varied in shape and may curve at an angle.

Delivery tube 30 can be substantially elongate and can extend from the proximal 26 to the distal end 24 of microcatheter 20. Tube 30 can generally run along the inner lumen of microcatheter 20 and may leave a space between its outer surface and the internal surface of microcatheter 20. In turn, delivery tube 30 and microcatheter 30 may be axially aligned. System 40 can deliver braid 10 to a location of interest (e.g. a lesion site) using microcatheter 20. In certain embodiments, microcatheter 20 can be pre-placed at a level of the aneurysm neck and used to track the device 1 to the lesion, for example by tracking marker band 44. Delivery tube 30 can be in mechanical connection with braid 10 at locking portion 54. As shown more particularly below, locking portion 54 can comprise or be a pusher ring. Braid 10 may be attached to locking portion 54 by slidable attachment, permanent attachment (e.g. crimped, laser, ultrasonic weld, or other sources of heat, adhesive, or the like) or other attachment approaches. When delivery tube 30 is mechanically attached to braid 10 at locking portion 54, distally translating, sliding, or otherwise moving tube 30 towards the aneurysm A can cause braid 10 to begin moving from the collapsed state within microcatheter 20 to its deployed state external to microcatheter 20 with segments 12 and 13.

In the deployed state, some or all of braid 10 is distal of microcatheter 20 so that segments 12, 13 can radially expand. Braid 10 is particularly advantageous as it is capable of being collapsed within microcatheter 20 while also being capable of forming multiple occlusive sacks in the deployed state. The mesh of braid 10 can be configured so that as braid 10 is distally translated and its end 14 exits from within microcatheter 20, segment 12 can radially expand to form an outer occlusive sack of the first porosity. The outer occlusive sack can be formed as end 14 slides away from end 24 of microcatheter 20.

As braid 10 is further distally translated, segment 13 can begin to radially expand internal to the outer occlusive sack of segment 12. By radially expanding inside segment 12, segment 13 can form an inner occlusive sack with a porosity greater than the porosity of segment 12, as shown in FIG. 2 whereby the respective sacks of segments 12, 13 are shown formed in a deployed state, segment 13 being internal to segment 12, but still connected to delivery tube 30 via locking portion 54. In FIG. 2, the distal end 14 can form the outer layer of the outer occlusive sack of segment 12 while the proximal end 16 can form the outer layer of the inner occlusive sack of segment 13.

As shown in FIG. 1B and FIG. 2, end 16 can be disposed on or adjacent marker band 44 and locking portion 54. The end 14 can be inserted through marker band 44 until proximal end 16 is disposed on or adjacent band 44 at locking portion 54. Locking portion 54 can then be connected to and/or folded over end 16. Braid 10 is not so limited and instead of being folded over, proximal end 16 can be operatively connected to locking portion 54 by sonic weld, mechanical attachment, or adhesive. Regardless of connection, the proximal end 16 being operatively connected to locking portion 54 can cause formation of an outer layer of the braid 10. When arranged and assembled with microcatheter 20 and a delivery tube 30, the device 1 can be delivered to the lesion site.

Turning to FIG. 3, an enlarged schematic side view of the braid 10 of FIGS. 1-2 is shown in a close-up, expanded state but not delivered to an aneurysm. As shown, each of segments 12 and 13 can have a generally spherical shaped segment associated with their respective occlusive sacks. While segment 12 of FIG. 3 shows that portions about and/or in communication with marker band 44 can be mirrored ellipsoids.

In practice, as shown in FIGS. 4A to 5B, the braid 10 can be pushed into the aneurysm A by the delivery tube 30 and be deployed with the lower porosity outer layer of segment 13 laying across the neck of the aneurysm A, and the inner layer of segment 12 can be expanding inside of the outer layer while pushing the outer layer in position against the aneurysm wall and aneurysm neck. In particular, FIGS. 4A to 5B depict an enlarged schematic side view of the delivery system 40 and braid 10 as the braid 10 is being pushed into an example aneurysm A. The outer diameter of segments 12, 13 can radially expand to a diameter greater than the microcatheter 20. Prior to the arrangement of FIG. 4A, the braid 10 can be assembled with a delivery tube 30 and/or a microcatheter 20 in a collapsed state. In this respect, the delivery system 40 and braid 10 can be packaged as a portable kit or system. The assembly between microcatheter 20, delivery tube 30, and/or braid 10 can take place before being introduced into the vasculature. The delivery system 40 used with braid 10, which can include microcatheter 20 and delivery tube 30, can be selectively positioned at the lesion site and delivery tube 30 can begin distally translating braid 10 towards the aneurysm.

Figure 4A:
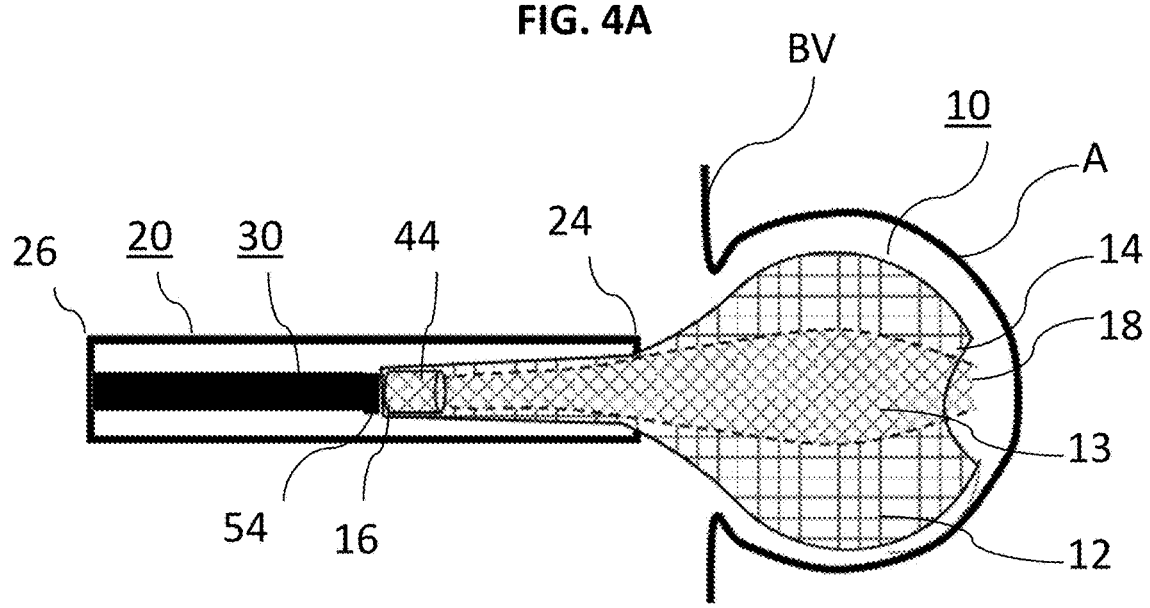
FIG. 4A is an enlarged schematic side view of the delivery system and braid of FIGS. 1-3 as the occlusive device is being pushed into an example aneurysm.

Turning to FIG. 4A, sack 12 has radially expanded towards the outer walls of aneurysm A while unexpanded portions proximal thereof of braid 10 continue to be translated by delivery tube 30. Braid 10 can expand as it as it distally moves away from end 24 of catheter 20 or upon its end 14 contacting aneurysm A. When expanding from the collapsed state to the state of FIG. 4A, segment 12 can radially expand to form the outer occlusive sack within aneurysm A. As shown in FIG. 4A, segment 12 can be a generally spherical shape internal to aneurysm A while segment 13 in turn remains mostly collapsed and stored within microcatheter 20. However, the portion of segment 13 distal of microcatheter 20 on or about its end 18 has begun to radially expand. Delivery tube 30 may include one or more fasteners operable to securely fasten braid 10 in place prior to deployment.

Figure 4B:
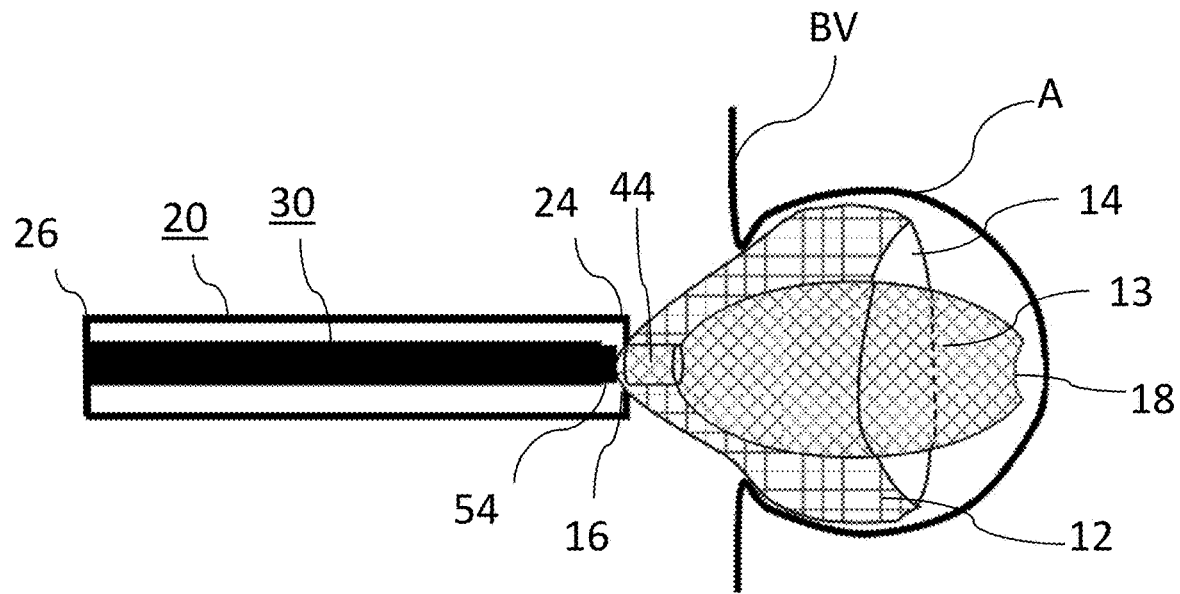
FIG. 4B is an enlarged schematic side view of the delivery system and braid of FIGS. 1-3 as the occlusive device is being pushed into an example aneurysm.

In FIG. 4B, the delivery tube 30 has distally slid braid 10 deeper into aneurysm A so that the outer surface of segment 12 has moved closer to dome D. Marker band 44 has been distally translated closer and tucked into the neck of aneurysm A. It is understood that the outer surface of braid 10 can be made from nitinol with interwoven platinum filaments for radiopacity. Delivery tube 30 may be driven by a hypotube from its proximal end 36 (not depicted) by an operator or the like. Microcatheter 20 may remain relatively stationary or fixed while delivery tube 30 can be seen distally translating braid 10 towards and through the neck of aneurysm A. Braid 10 can include a pre-weakened or transition portion 19 (e.g., depicted in FIGS. 1A-1B) so that as braid 10 and delivery tube 30 are distally translated away from microcatheter 20 and deeper into aneurysm A, segments 12 can also translate causing radial expansion and formation of their respective occlusive sacks. In certain embodiments, portion 19 shown in FIG. 1 can initiate radial expansion of segment 13 inside segment 12. For example, translation of braid 10 a first predetermined distance can cause segment 12 to radially expand to form its outer occlusive sack. Further translating braid a second predetermined distance into aneurysm A, as is shown in FIG. 4B can cause the inner occlusive sack of segment 13 to form inside of the outer occlusive sack.

Figure 5A:
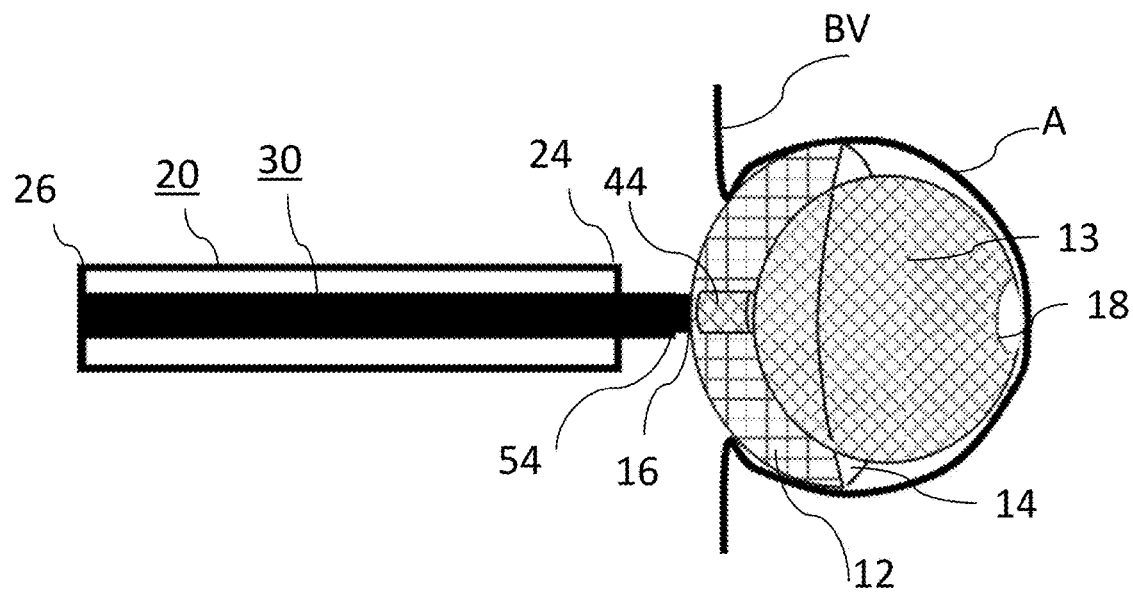
FIG. 5A is an enlarged schematic side view of the delivery system and braid of FIGS. 1-3 as the occlusive device is being pushed into an example aneurysm.

In FIG. 5A, the delivery tube 30 is distally translated deeper into aneurysm A. Moving between FIGS. 4A to 5A, it is shown that distally translating the braid 10, by the delivery tube 30, deeper into aneurysm A can cause segment 12 to further radially expand. Further distal translation also can cause band 44 to further tuck into braid 10, including segments 12, 13, which can cause the proximal portion of segment 12 adjacent or in communication with the neck of the aneurysm to become more spherical. In certain embodiments, the widening of segment 12 between FIGS. 4A and 5A can cause end 14 to slide proximally back towards end 24 of microcatheter while segment 13 continues to expand radially. For example, as end 14 of segment 12 expands to a larger diameter between FIGS. 4A and 5A, end 14 may also be drawn proximally from end 18 yet expand outwardly while end 18 may remain on or adjacent the dome of the aneurysm.

As also seen moving between FIGS. 4A to 5A, the junction between end 16 of braid 10, locking portion 54, and delivery tube 30 can move from within microcatheter 20 in the collapsed state to completely within aneurysm A in the deployed state. Once braid 10, including segments 12 and 13, are selectively positioned and arranged to the desired condition (e.g. braid 10 has been translated distally to expand segments 12, 13 to form the outer and inner sacks and/or braid 10 has expanded to a predetermined packing density), the outer occlusive sack of segment 12 can be seen being sealed against the aneurysm neck with its porosity being lower than the porosity of segment 13 to deflect, divert or slow flow into the aneurysm. At this point, braid 10 can be detached from the delivery tube 30 as shown in FIG. 5B. In other words, as the braid 10 is distally translated towards the dome of the aneurysm A, segments 12, 13 can expand and be used to support the aneurysm wall in a manner that is easy, efficient, and avoids risks of rupture (e.g., see also FIGS. 8G-8H).

Figure 5B:
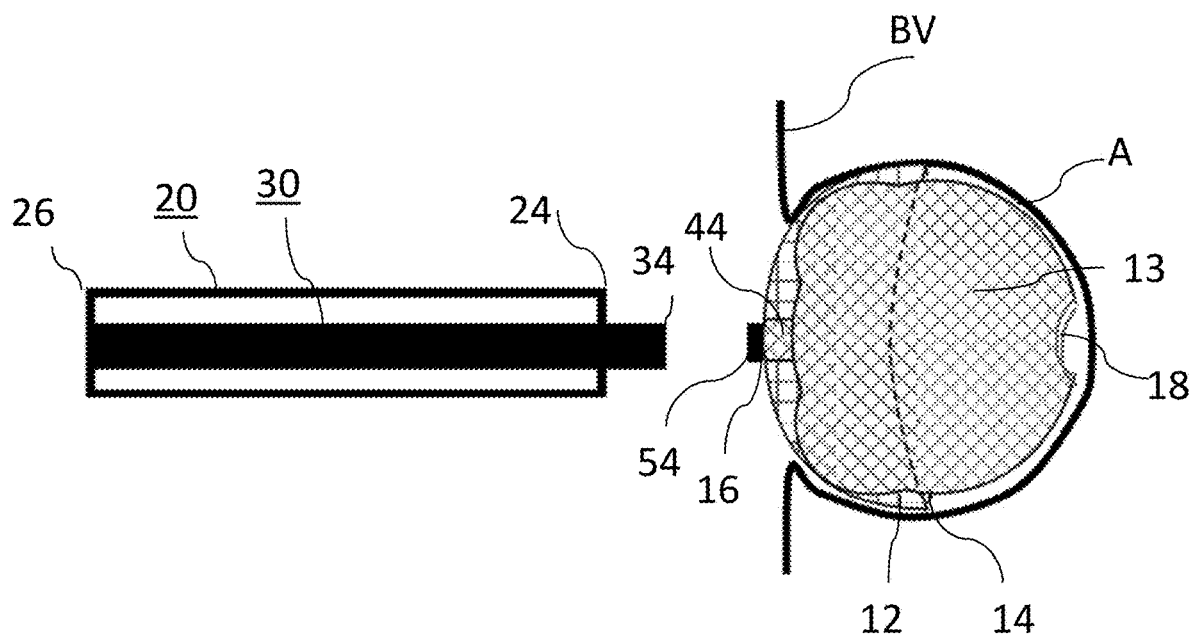
FIG. 5B is an enlarged schematic side view of the delivery system and braid of FIGS. 1-3 after the occlusive device is deployed into an example aneurysm.

Once expanded and positioned, delivery tube 30 can be proximally translated back into microcatheter 20 and retracted from the braid 10 and aneurysm A. FIG. 5B shows an example arrangement of braid 10 in its expanded state and the inner and outer sacks of segments 13 and 12, respectively, completely formed with delivery tube 30 having detached from locking portion 54. FIG. 5B merely shows example spherical sacks of segments 12, 13 fully formed in a manner sufficient to occlude aneurysm. However, if either sack of segments 12, 13 is not precisely positioned or need to be reset or adjusted within aneurysm A for safe occlusion without risk of rupture, braid 10 can be retracted back into microcatheter 20 by proximally withdrawing delivery tube 30 while still attached to braid 10.

In FIG. 5B, since the sacks of segments 12, 13 have been selectively positioned and formed within aneurysm A, braid 10 has been detached from delivery tube 30 and delivery tube 30 and microcatheter 20 can now be retraced from aneurysm A and the lesion site. Marker band 44 and locking portion 54 has also distally translated so that it is positioned on or adjacent the neck of the aneurysm A. Expanding segments 12, 13 and tucking band 44 and/or locking portion 54 into the braid 10 is particularly advantageous as it can prevent braid 10 from creating a protrusion that would otherwise extend into the parent vessel. Instead, any such protrusion can now be tucked into segment 12. Arranging braid 10 in this manner across the neck of the aneurysm while also varying the porosity of segments 12, 13 can create a flow diversion essentially inside of the sacks of braid 10.

Figure 6A:
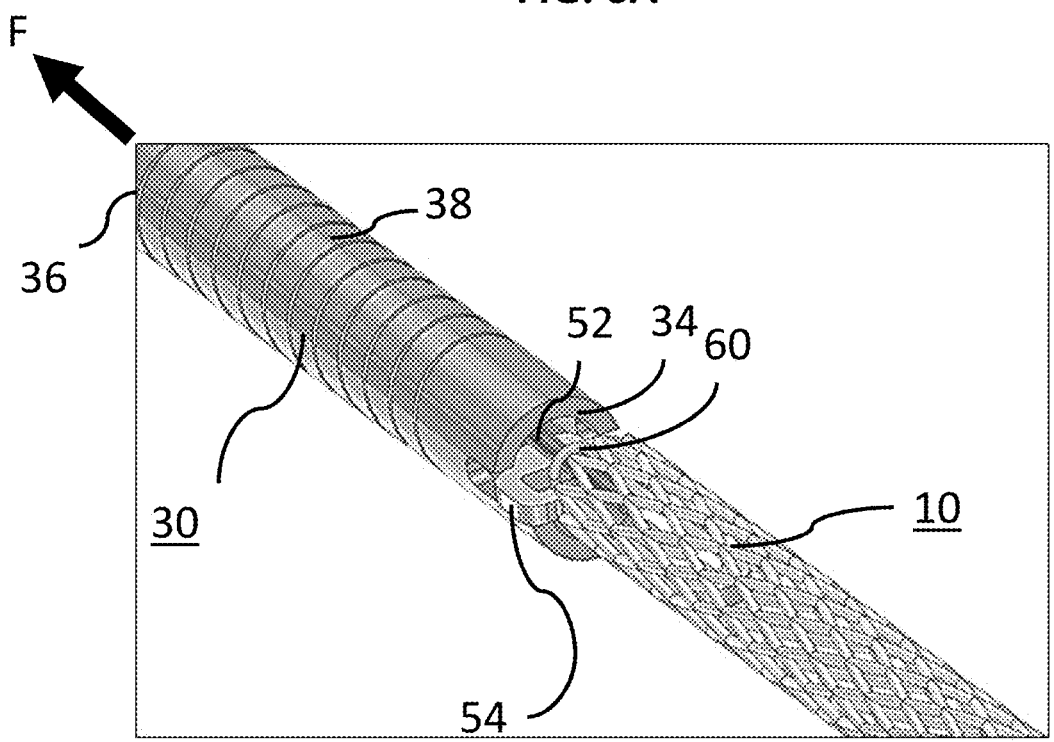
FIG. 6A is a perspective schematic view showing an exemplary delivery system for use with an example occlusive device.

FIGS. 6A to 7B generally illustrate example attachment and delivery between delivery tube 30 and braid 10 for deploying and detaching braid 10 in aneurysm A. The embodiments of FIGS. 6A to 7B is merely one way that delivery tube 30 and braid 10 may be attached at end 34 and any number of attachment means are contemplated as needed or required. The delivery tube 30 as shown can have a lumen extending from a proximal end 36 to a distal, delivery end 34. FIG. 6A illustrates braid 10 engaged with the locking member 52 and loop wire 58 locked into the locking portion 54. The opening 60 of the loop wire 58 can be placed through the locking portion 54. The locking portion 54 preferably takes the form of a small diameter elongate filament, however, other forms such as wires or tubular structures are also suitable. While the locking portion 54 is preferably formed of nitinol, other metals and materials such as stainless steel, PTFE, nylon, ceramic or glass fiber and composites may also be suitable. Locking member 52, in one example, may be an elongated retractable fiber that may extend between ends 24 and 26 of the microcatheter 20. Locking member 52 preferably takes the form of a small diameter elongate filament, however, other forms such as wires or tubular structures are also suitable. While the locking member 52 is preferably formed of nitinol, other metals and materials such as stainless steel, PTFE, nylon, ceramic or glass fiber and composites may also be suitable. When the locking member 52 is put through the opening 60 the braid 10 is now secure. It is understood that delivery tube 30 may include a compressible portion 38 disposed between its ends 34 and 36.

The compressible portion 38 can allow the delivery tube 30 to bend and/or flex. Such flexibility can assist tracking the braid 10 through the microcatheter 20 and the tortuous path through the vasculature. The compressible portion 38 can be formed with interference spiral cuts that can allow for gaps to permit bending but in one example, do not act as a spiral-cut spring. Compressible portion 38 can be axially adjustable between an elongated condition and a compressed condition. However, any other arrangement allowing axial adjustment (e.g., a wound wire or spiral ribbon) can also be suitable for use with detachment systems according to the present disclosure). The compressible portion 38 can be in the elongated condition at rest and automatically or resiliently returns to the elongated condition from a compressed condition, unless otherwise constrained. The function of the compressible portion 38 is described in greater detail herein.

Figure 6B:
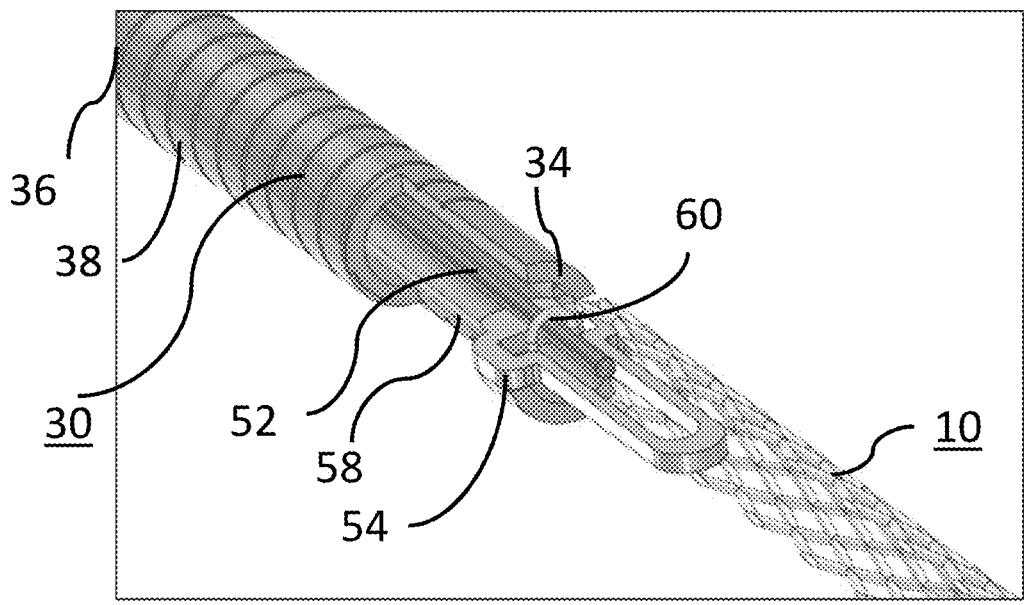
FIG. 6B is a perspective schematic view of FIG. 6A but with partial cross-section of the delivery system and the occlusive device.
Figure 7A:
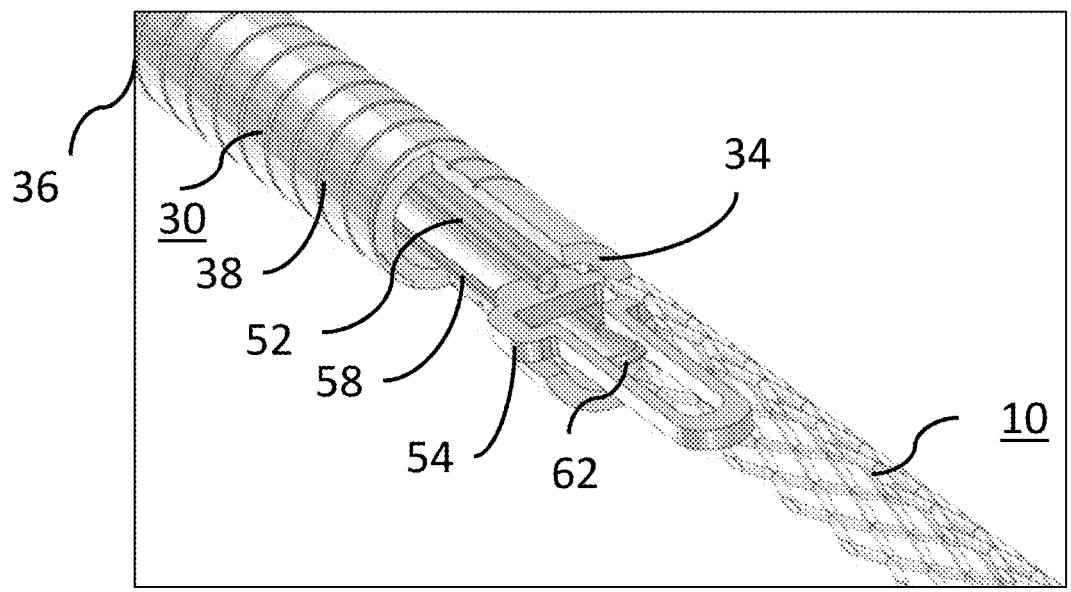
FIG. 7A is a perspective schematic view of FIGS. 6A-6B being deployed with partial cross-section of the delivery system and the occlusive device.
Figure 7B:
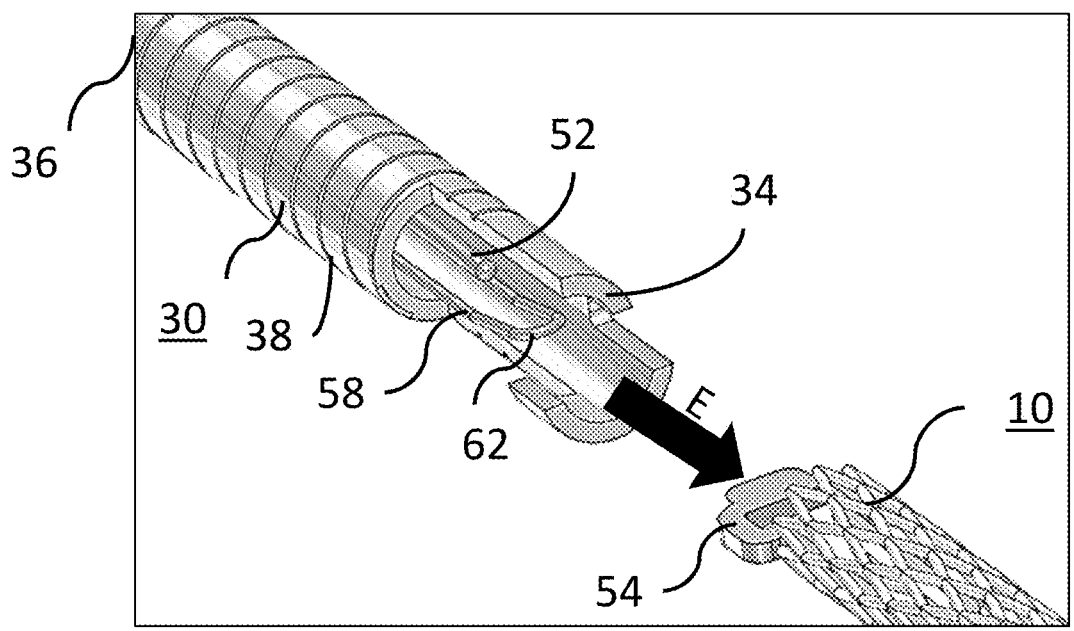
FIG. 7B is a perspective schematic view of FIGS. 6A-6B deployed with the exemplary delivery system detached from the occlusive device.

As shown in FIG. 6A, force F was previously applied to place the delivery tube 30 in a compressed state. FIG. 6B illustrates the locking member 52 being drawn proximally to begin the release sequence for braid 10. FIG. 7A illustrates the instant the locking member 52 exits the opening 60 and is pulled free of the loop wire 58. The distal end 62 of the loop wire 58 falls away/returns to its preformed shape and exits the locking portion 54. As can be seen, there is now nothing holding the braid 10 to the delivery tube 30. FIG. 7B illustrates the end of the release sequence. Here, the compressible portion 38 of the delivery tube 30 has expanded/returned to its original shape and "sprung" forward. An elastic force E is imparted by the distal end 34 of the delivery tube 30 to the braid 10 to "push" it away to insure a clean separation and delivery of the braid 10 to the aneurysm A. It is to be understood that the delivery scheme described in FIGS. 6A-7B are merely example approaches to delivery of braid 10.

Figure 8A:
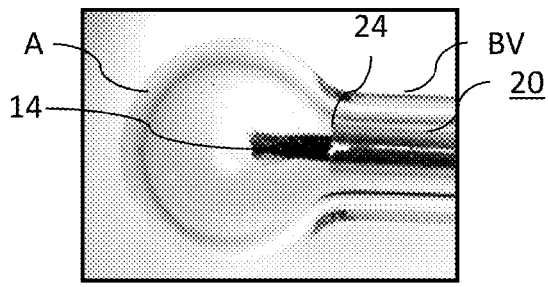
FIG. 8A is an enlarged view one step of an exemplary delivery system device being deployed into an aneurysm in accordance with this disclosure, wherein the system is shown moving from a collapsed condition to a deployed condition.
Figure 8E:
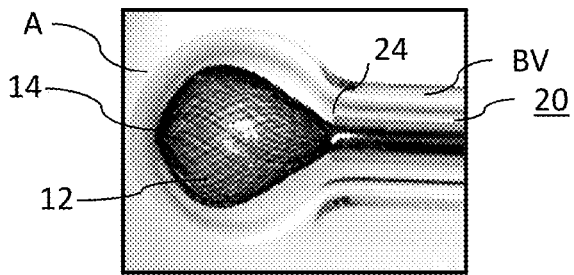
FIG. 8E is an enlarged view one step of an exemplary delivery system device being deployed into an aneurysm in accordance with this disclosure, wherein the system is shown moving from a collapsed condition to a deployed condition.
Figure 8B:
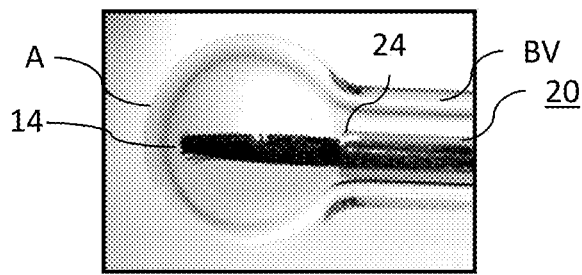
FIG. 8B is an enlarged view one step of an exemplary delivery system device being deployed into an aneurysm in accordance with this disclosure, wherein the system is shown moving from a collapsed condition to a deployed condition.
Figure 8F:
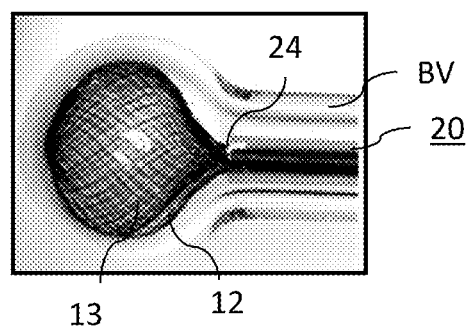
FIG. 8F is an enlarged view one step of an exemplary delivery system device being deployed into an aneurysm in accordance with this disclosure, wherein the system is shown moving from a collapsed condition to a deployed condition.
Figure 8C:
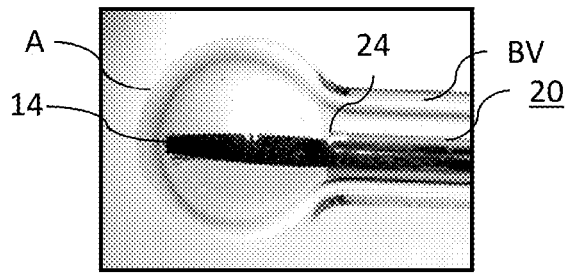
FIG. 8C is an enlarged view one step of an exemplary delivery system device being deployed into an aneurysm in accordance with this disclosure, wherein the system is shown moving from a collapsed condition to a deployed condition.
Figure 8G:
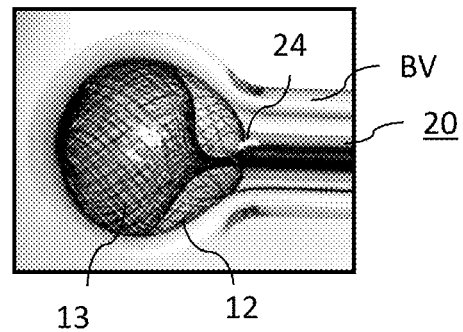
FIG. 8G is an enlarged view one step of an exemplary delivery system device being deployed into an aneurysm in accordance with this disclosure, wherein the system is shown moving from a collapsed condition to a deployed condition.
Figure 8D:
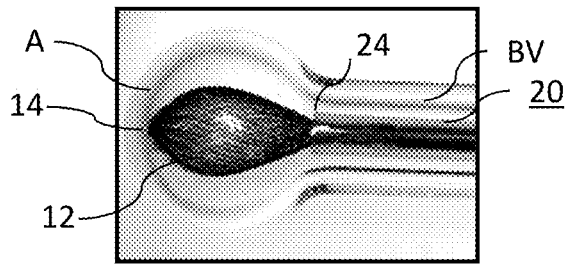
FIG. 8D is an enlarged view one step of an exemplary delivery system device being deployed into an aneurysm in accordance with this disclosure, wherein the system is shown moving from a collapsed condition to a deployed condition.

FIGS. 8A-8H depict example embodiments of braid 10 being deployed and delivered to an example aneurysm A. Specifically, in FIG. 8A, braid 10 can be seen being initially advanced into aneurysm A. End 24 of microcatheter 20 has been selectively positioned at the neck of aneurysm A while end 14 of braid 10 is being advanced distally towards aneurysm A and away from end 24 of microcatheter 20. In FIGS. 8B-8C, end 14 of braid 10 continues to be distally advanced towards dome D of aneurysm A while microcatheter 20 remains generally stationary until as seen in FIGS. 8D to 8E, end 14 of braid 10 contacts dome D and segment 12 begins radially expanding to form the outer occlusive sack of braid 10. In FIG. 8C in particular, the outer occlusive sack of segment 12 is nearly fully formed as braid 10 has continued its distal translation into aneurysm A. In FIG. 8D, braid 10 continues to be distally translated until its outer occlusive sack of segment 12 is fully formed. In FIG. 8D specifically, it can be seen that the outer occlusive sack of segment 12 is now adjacent and supporting dome D. Braid 10 meanwhile may continue to be translated to form inner occlusive sack of segment 13. The inner occlusive sack of segment 13 as shown can overlay sack 12 for additional stability. Further, by having segment 12 contact dome D causes segment 12 to begin to take shape as braid 10 expands.

Figure 8H:
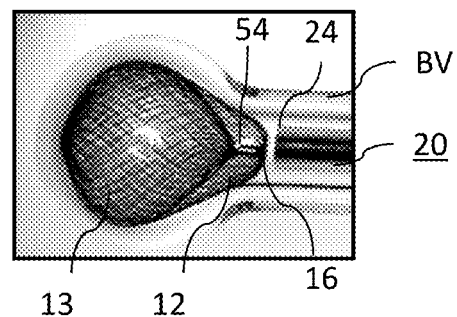
FIG. 8H is an enlarged view one step of an exemplary delivery system device being deployed into an aneurysm in accordance with this disclosure, wherein the system is shown moving from a collapsed condition to a deployed condition.
Figure 9:
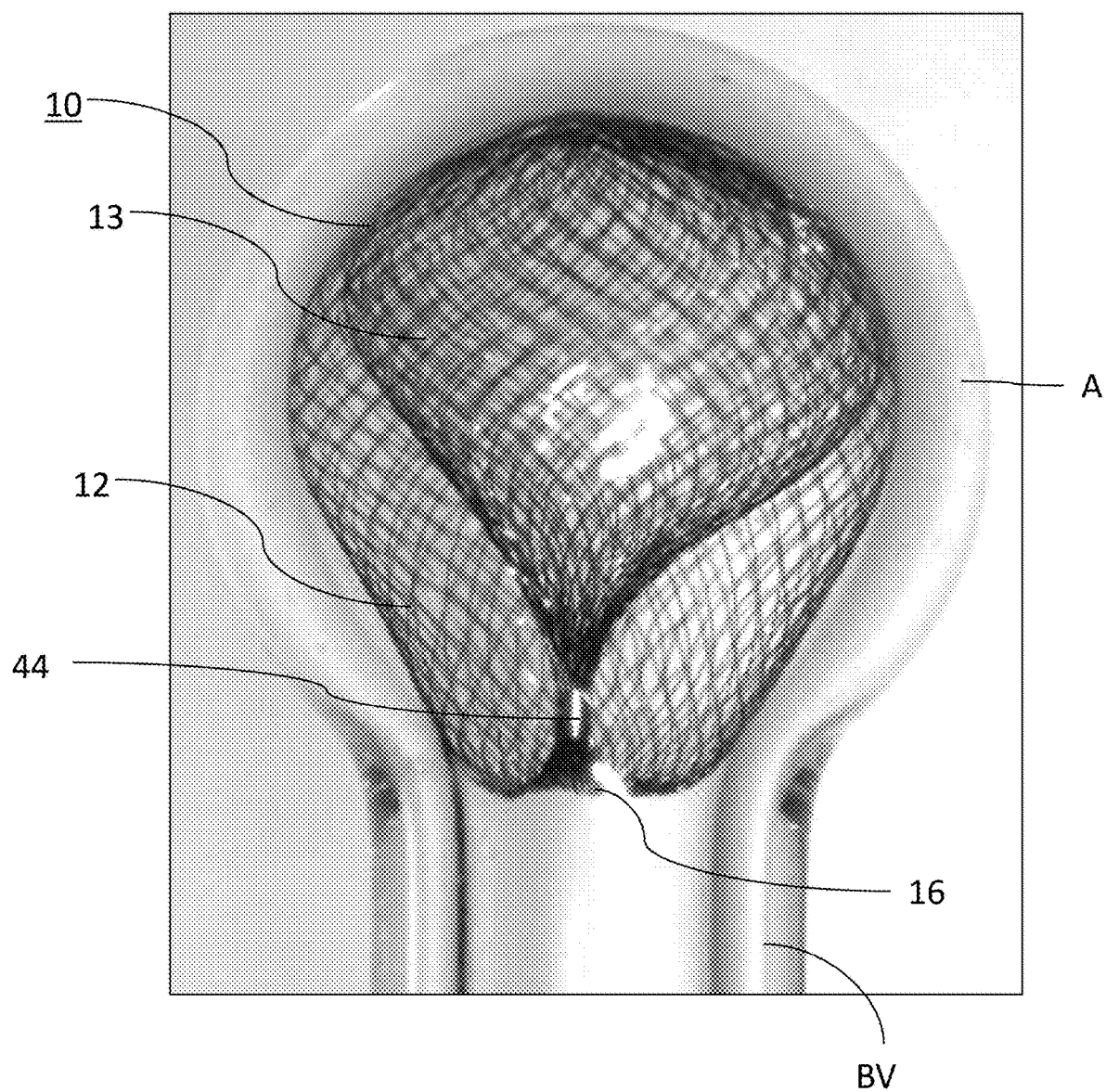
FIG. 9 depicts an example braid of this disclosure deployed in an example aneurysm.
Figure 10A:
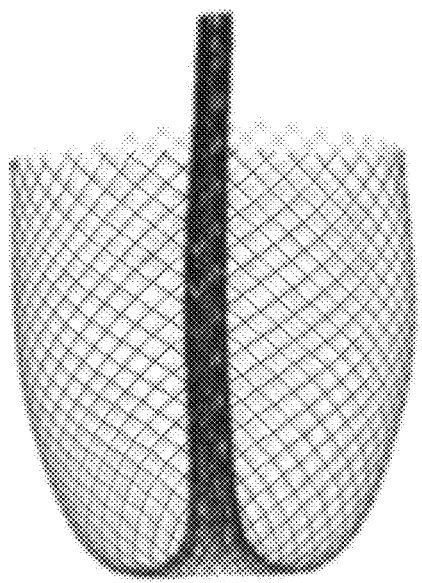
FIG. 10A depicts an example prototype braid of this disclosure.
Figure 10B:
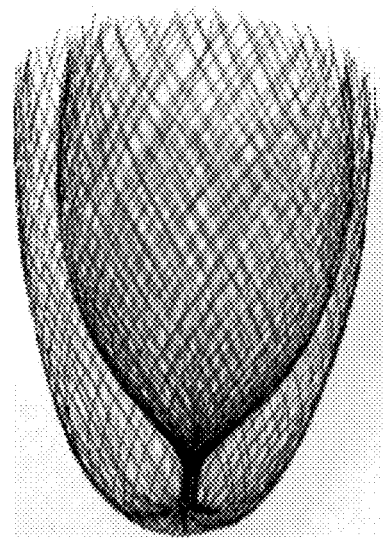
FIG. 10B depicts an example prototype braid of this disclosure.
Figure 10C:
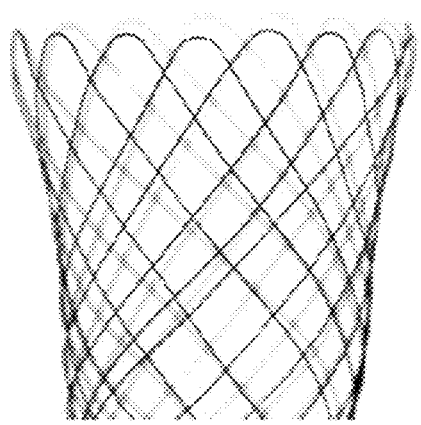
FIG. 10C depicts an example prototype braid of this disclosure.
Figure 10D:
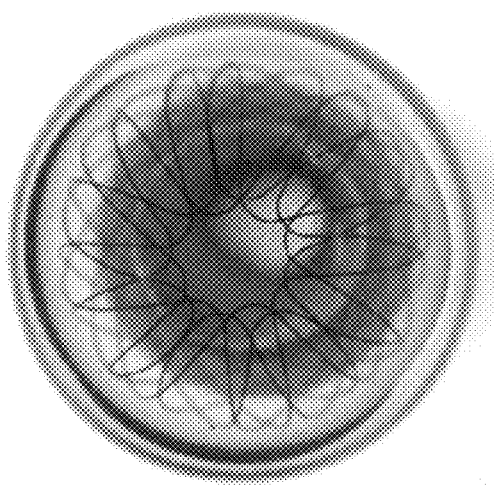
FIG. 10D depicts an example prototype braid of this disclosure.

In FIG. 8F, braid 10 continues to be pushed into the aneurysm wall causing the inner occlusive sack of segment 13 to continue to expand while the outer occlusive sack of segment 12 continues to expand along the aneurysm wall. In FIG. 8G, braid 10 continues its distal translation whereby the inner occlusive sack of segment 13 has been formed inside the outer occlusive sack and its based end has been pushed further into the segment 12, similar to coil packing. It is understood that any number of inner occlusive sacks can be positioned internal to segment 12 (e.g. by providing one or more additional segments capable of forming inner occlusive sacks) and the one or more additional inner occlusive sacks can be formed as braid 10 is distally translated into aneurysm A. A packing density of braid 10 can also be tailored or adjusted as braid 10 is distally translated to form the inner occlusive sack of segment 13 overlaid internal to sack 12. For example, when comparing the arrangement of FIG. 8F versus 8G, the stem portion aft of the inner occlusive sack of segment 13 can act to "pack" the outer occlusive sack of segment 12 as it is distally translated. In FIG. 8H, braid 10 has been distally translated to the desired depth in aneurysm A and now locking portion 54 is visible as being external to microcatheter 20 and at or adjacent the neck of aneurysm A. Since braid 10 and corresponding segments 12 and 13 are now selectively positioned, expanded, and arranged within aneurysm A, delivery tube 30 and microcatheter 20 can be released from braid 10 and proximally translated away from the aneurysm A. By arranging segments 12 and 13 as shown in FIGS. 8A-8H and forming the outer occlusive sack of segment 12 with a lower porosity than the inner occlusive sack of segment 13, the braid 10 can induce a flow diverting effect across the neck of the aneurysm.

FIGS. 10A-10D depict example prototype braids with varying braid properties. These prototypes are strictly for illustrative purposes.

FIG. 11 is a flow diagram for a method 1100 of delivering an occlusive device to the aneurysm. Step 1105 includes slidably positioning a delivery tube within a microcatheter. Step 1110 includes slidably positioning an expandable and inwardly invertible braid within the microcatheter, the braid being in a collapsed state within the microcatheter and comprising a distal end and a proximal end. Step 1115 includes detachably attaching the proximal end of the braid to the distal end of the delivery tube. Step 1120 includes selectively positioning the microcatheter, the delivery tube, and the braid into vasculature of the aneurysm. For example, the microcatheter can position the braid and the delivery tube at the neck of the aneurysm. Step 1125 includes distally sliding the braid, by the delivery tube, towards the aneurysm. Prior to step 1125, the distal end of the braid can be inserted through a marker band until a proximal end of the braid is on or adjacent the marker band. Step 1130 includes distally pushing the braid, by the delivery tube, into the aneurysm sack whereby the braid radially expands to form an outer occlusive sack with a lower porosity operable to lay across the neck of the aneurysm. The outer occlusive sack can form upon or as the distal end of the braid is moved distally from the microcatheter and in communication with a dome of the aneurysm.

Step 1135 includes expanding an inner layer of the braid inside of the outer occlusive sack while distally pushing the outer occlusive sack against the aneurysm wall and aneurysm neck. The inner layer that expands inside the outer occlusive sack can form an inner occlusive sack and be formed by folding the proximal end over the marker band and then distally pushing the braid into the aneurysm as described. The porosity of the inner occlusive sack can be greater than the porosity of the outer occlusive sack. Step 1140 includes releasing the occlusive device, including the outer and inner occlusive sacks, and withdrawing the delivery tube and the microcatheter from the aneurysm. By varying the porosities of portions of the braid, when installed in the aneurysm and detached from the delivery system, the braid can induce a flow diverting effect across the neck of the aneurysm.

FIG. 12 is a flow diagram for a method 1200 of occluding an aneurysm. Step 1205 includes positioning a radially expandable braid within vasculature of the aneurysm. Step 1210 includes forming a first radially expandable segment of the braid with a porosity lower than a porosity of a second radially expandable segment. Step 1215 includes distally pushing the braid into the aneurysm whereby the first radially expandable segment radially expands to form an outer occlusive sack. Step 1220 includes further distally pushing the braid thereby expanding the second radially expandable segment inside of the outer occlusive sack. Step 1225 includes positioning the first radially expandable segment adjacent or in communication with a neck of the aneurysm. Step 1230 includes deflecting, diverting or slowing flow into the aneurysm across the neck of the aneurysm when the outer occlusive sack is formed across the neck and the inner occlusive sack is formed therein.

It is understood that variations of the braid 10 can include various materials such as stainless steel, bio absorbable materials, and polymers. Braid 10, including any specific portions such as any breaks, varying regions of differing porosities, and occlusive sacks, can be heat set to various configurations such as spherical, oblong, saddle shaped, or the like, for the purpose of shaping the outer and/or inner sack to better match the aneurysm morphology. In addition, the braid 10 can be heat shaped to include weak points to facility the radial expansion of the occlusive sacks. Further, interstices of braid 10 that form the sacks can vary, or be selectively designed, in size or shape along its length depending on how much braid 10 is caused to radially expand as delivery tube 30 is distally moved.

The specific configurations, choice of materials and the size and shape of various elements can be varied according to particular design specifications or constraints requiring a system or method constructed according to the principles of the disclosed technology. Such changes are intended to be embraced within the scope of the disclosed technology. The presently disclosed embodiments, therefore, are considered in all respects to be illustrative and not restrictive. It will therefore be apparent from the foregoing that while particular forms of the disclosure have been illustrated and described, various modifications can be made without departing from the spirit and scope of the disclosure and all changes that come within the meaning and range of equivalents thereof are intended to be embraced therein.

What is claimed is:

1. An occlusive device for treating an aneurysm, comprising:
 a braid comprising a mesh and being translatably disposable within a microcatheter from a collapsed state to a deployed state;
 wherein in the deployed state, the mesh of the braid comprises:
  an outer occlusive sack comprising a proximal end and a distal end, the outer occlusive sack capable of pushing against an aneurysm wall of the aneurysm; and
  an inner occlusive sack comprising a proximal end and a distal end, the inner occlusive sack disposed inside the outer occlusive sack, the proximal ends of the inner and outer occlusive sacks aligned with each other in both the collapsed and deployed states, the distal ends of each sack being positioned on equivalent sides opposite the proximal ends of each sack in both the collapsed and deployed states, and the braid configured so that distally translating the braid in the aneurysm as the outer occlusive sack is forming causes an inner layer of the braid inside of the outer occlusive sack to radially expand inside the outer occlusive sack and form the inner occlusive sack.

2. The device of claim 1, wherein a porosity of the inner occlusive sack is greater than a porosity of the outer occlusive sack.

3. The device of claim 2, wherein in the deployed state, the outer occlusive sack is capable of sealing against the neck of the aneurysm.

4. The device of claim 1, wherein the inner layer of the braid is capable of radially expanding inside the outer occlusive sack while the outer occlusive sack is pushed against the aneurysm wall and aneurysm neck.

5. The device of claim 1, further comprising a marker band in communication with a proximal end of the braid, wherein the inner layer that radially expands inside the outer occlusive sack is formed by folding the proximal end of the braid over the marker band.

6. The device of claim 1, wherein in the deployed state, the braid is detachable from a delivery system in the aneurysm.

7. The device of claim 6, further comprising the delivery system, wherein the delivery system comprising:

a microcatheter; and a delivery tube comprising a distal end and a proximal end, the distal end of the delivery tube being detachably connected to the proximal end of the braid, the delivery tube being translatably disposable within the microcatheter;

wherein the delivery tube is capable of distally translating the braid within the microcatheter from the collapsed state to the deployed state.

8. The device of claim 1, wherein the outer occlusive sack comprises fewer wire segments than the inner occlusive sack.

9. A braid for treating an aneurysm, the braid comprising:

a first radially expandable mesh segment comprising a proximal end and an open distal end and operable to move from a collapsed state within a microcatheter to a deployed state distal of the microcatheter, wherein the first radially expandable segment is capable of radially expanding to form an outer occlusive sack in the aneurysm in the deployed state that is sealable against a neck of the aneurysm;

a second radially expandable mesh segment comprising a proximal end and an open distal end and operable to move from the collapsed state within the microcatheter to the deployed state distal of the microcatheter, wherein the second radially expandable mesh segment is capable of radially expanding inside the outer occlusive sack to form an inner occlusive sack in the outer occlusive sack in the deployed state, the proximal ends of each expandable mesh segment aligned with each other in both the collapsed and deployed states, and the distal ends of each expandable mesh segment being positioned on equivalent sides opposite the proximal ends of each expandable mesh segment in both the collapsed and deployed states the braid configured so that distally translating the braid in the aneurysm as the outer occlusive sack is forming causes an inner layer of the braid inside of the outer occlusive sack to radially expand inside the outer occlusive sack and form the inner occlusive sack.

10. The braid of claim 9, the braid is detachably deployable by a delivery system to an aneurysm.

11. The braid of claim 9, the braid further comprising a buckle portion disposed between the first and second radially expandable segments, the buckle portion permitting the inner occlusive sack to be formed within, overlaid with, and expand in the outer occlusive sack.

12. The braid of claim 9, wherein dimensions of interstices of the braid vary at a proximal end versus a distal end so that a porosity of the outer occlusive sack is less than a porosity of the inner occlusive sack when positioned across the neck of the aneurysm.

13. A method of occluding an aneurysm, comprising:

positioning a radially expandable braid according to claim 9 into vasculature of the aneurysm;

forming the first radially expandable segment of the braid with a porosity lower than a porosity of the second radially expandable segment;

distally pushing the braid into the aneurysm whereby the first radially expandable segment radially expands to form the outer occlusive sack;

further distally pushing the braid thereby expanding the second radially expandable segment inside of the outer occlusive sack;

positioning the first radially expandable segment adjacent or in communication with a neck of the aneurysm;

deflecting, diverting or slowing flow into the aneurysm across the neck of the aneurysm when the outer occlusive sack is formed across the neck and the inner occlusive sack is formed therein.

14. A method of delivering an occlusive device to an aneurysm, comprising:

slidably positioning a delivery tube within a microcatheter;

positioning a radially expandable braid according to claim 9 within the microcatheter, the braid being in a collapsed state within the microcatheter and comprising a distal end and a proximal end;

attaching the proximal end of the braid to the distal end of the delivery tube;

selectively positioning the microcatheter, the delivery tube, and the braid into vasculature of the aneurysm;

distally sliding the braid from the microcatheter, by the delivery tube, towards the aneurysm;

distally pushing the braid, by the delivery tube, into the aneurysm whereby the first radially expandable segment of the braid radially expands to form the outer occlusive sack, the outer occlusive sack being operable to lay across a neck of the aneurysm;

further distally pushing the braid thereby expanding the second radially expandable segment inside of the outer occlusive sack while distally pushing the outer occlusive sack against the aneurysm wall and the neck of the aneurysm; and releasing the braid, including the outer and inner occlusive sacks, and withdrawing the delivery tube and the microcatheter from the aneurysm.

15. The method of claim 14, further comprising:

forming the first radially expandable segment with a porosity lower than a porosity of the second radially expandable segment;

positioning the first radially expandable segment adjacent or in communication with the neck of the aneurysm; and deflecting, diverting or slowing flow into the aneurysm across the neck of the aneurysm when the outer occlusive sack is formed across the neck and the inner occlusive sack is formed therein.

16. The method of claim 14, wherein the inner occlusive sack comprises the inner layer of the braid.

* * * * *